(12) United States Patent
Montenegro et al.

(10) Patent No.: US 9,050,395 B2
(45) Date of Patent: Jun. 9, 2015

(54) MEDICAL PRODUCT COMPRISING A CHITOSAN-COATED WALL AND METHOD FOR MANUFACTURING A MEDICAL PRODUCT

(75) Inventors: Rivelino Montenegro, Mainz (DE); Thomas Freier, Mainz (DE)

(73) Assignee: Medovent GmbH, Mainz (DE)

( * ) Notice: Subject to any disclaimer, the term of this patent is extended or adjusted under 35 U.S.C. 154(b) by 710 days.

(21) Appl. No.: 13/322,870

(22) PCT Filed: May 29, 2009

(86) PCT No.: PCT/EP2009/056685
§ 371 (c)(1),
(2), (4) Date: Apr. 25, 2012

(87) PCT Pub. No.: WO2010/136075
PCT Pub. Date: Dec. 2, 2010

(65) Prior Publication Data
US 2012/0203326 A1    Aug. 9, 2012

(51) Int. Cl.
*A61F 2/82*  (2013.01)
*C25D 3/02*  (2006.01)
(Continued)

(52) U.S. Cl.
CPC ............... *A61L 31/16* (2013.01); *A61L 31/042* (2013.01); *A61L 31/10* (2013.01); *A61L 2300/606* (2013.01); *C25D 13/12* (2013.01)

(58) Field of Classification Search
CPC ....... A61L 31/042; A61L 21/10; C25D 13/12
USPC ............. 427/2.1, 2.24, 2.25, 230, 239, 430.1; 205/131, 316
See application file for complete search history.

(56) References Cited

U.S. PATENT DOCUMENTS 6,517,888 B1 *  2/2003  Weber .......................... 427/2.24
2005/0149177 A1 *  7/2005  Weber et al. ................. 623/1.46

FOREIGN PATENT DOCUMENTS

JP    2007-505703 A    3/2007
JP    2009-501828 A    1/2009
(Continued)

OTHER PUBLICATIONS

Thierry, Benjamin et al., "Bioactive Coatings of Endovascular Stents Based on Polyelectrolyte Multilayers", 2003 Biomacromolecules vol. 4, No. 6 (pp. 1564-1571).
(Continued)

*Primary Examiner* — Cachet Sellman
(74) *Attorney, Agent, or Firm* — Harris Beach PLLC

(57) ABSTRACT

A method for manufacturing a medical product comprising a hollow body (2), wherein at least part of a wall of the hollow body (2) is coated at least on the inside with a layer comprising a polymer; at least the part of at least the inside of the wall of the medical product is brought into contact with a mixture (6) of the polymer and the polymer is deposited from the mixture (6) on at least the part of the inside of the wall. And a medical product comprising a hollow body (2) with a wall consisting of one or more structural elements (16), at least a section of the wall being coated with a layer (15) comprising native chitosan, wherein both on the inside and the outside of the hollow body (2) at least some of the one or more structural elements (16) of the wall of the hollow body (2) are at least partly coated with the native chitosan layer (15). And a method for electrodepositing a polymer on an electrode from an acidic mixture of the polymer, wherein the mixture (6) comprises a multibasic acid.

8 Claims, 8 Drawing Sheets

(51) Int. Cl.
  *B05D 7/00* (2006.01)
  *A61L 31/16* (2006.01)
  *A61L 31/04* (2006.01)
  *A61L 31/10* (2006.01)
  *C25D 13/12* (2006.01)

(56) References Cited

FOREIGN PATENT DOCUMENTS

| WO | WO-01 14617 A1 | | 3/2001 |
|---|---|---|---|
| WO | WO 0114617 A1 | * | 3/2001 |
| WO | WO-2005027794 A2 | | 3/2005 |
| WO | WO-2007010536 A2 | | 1/2007 |
| WO | WO-2009154961 A2 | | 12/2009 |

OTHER PUBLICATIONS

Notification of Transmittal of International Search Report and International Search Report for PCT/EP09/56685 (5 pages).

Wu, Li-Qun et al., "Voltage-Dependent Assembly of the Polysaccharide Chitosan onto an Electrode Surface", 2002 Langmuir, vol. 18, No. 22 (pp. 8620-8625).

Fernandes, Rohan et al., "Electrochemically Induced Deposition of a Polysaccharide Hydrogel onto a Patterned Surface", 2003 Langmuir vol. 19, No. 10 (pp. 4058-4062).

* cited by examiner

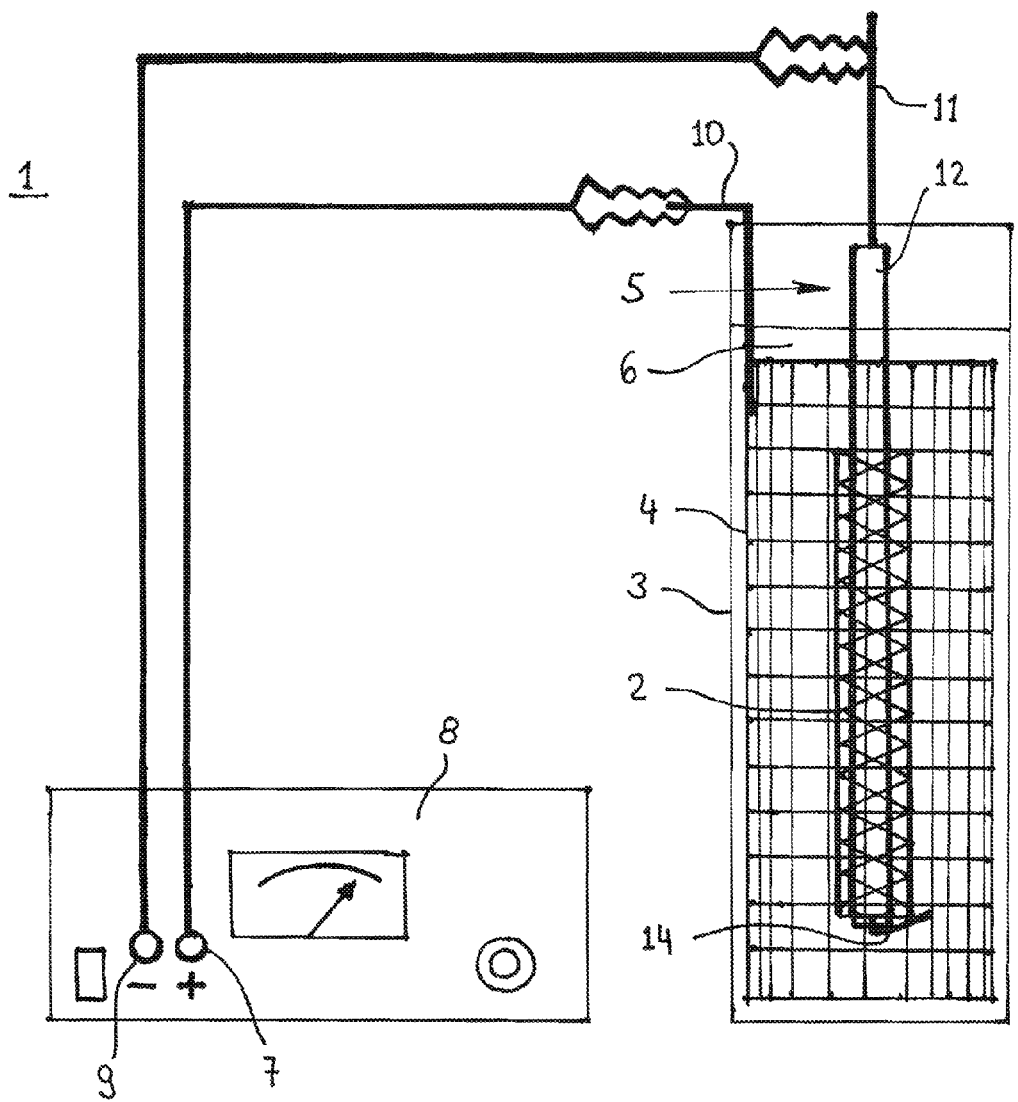

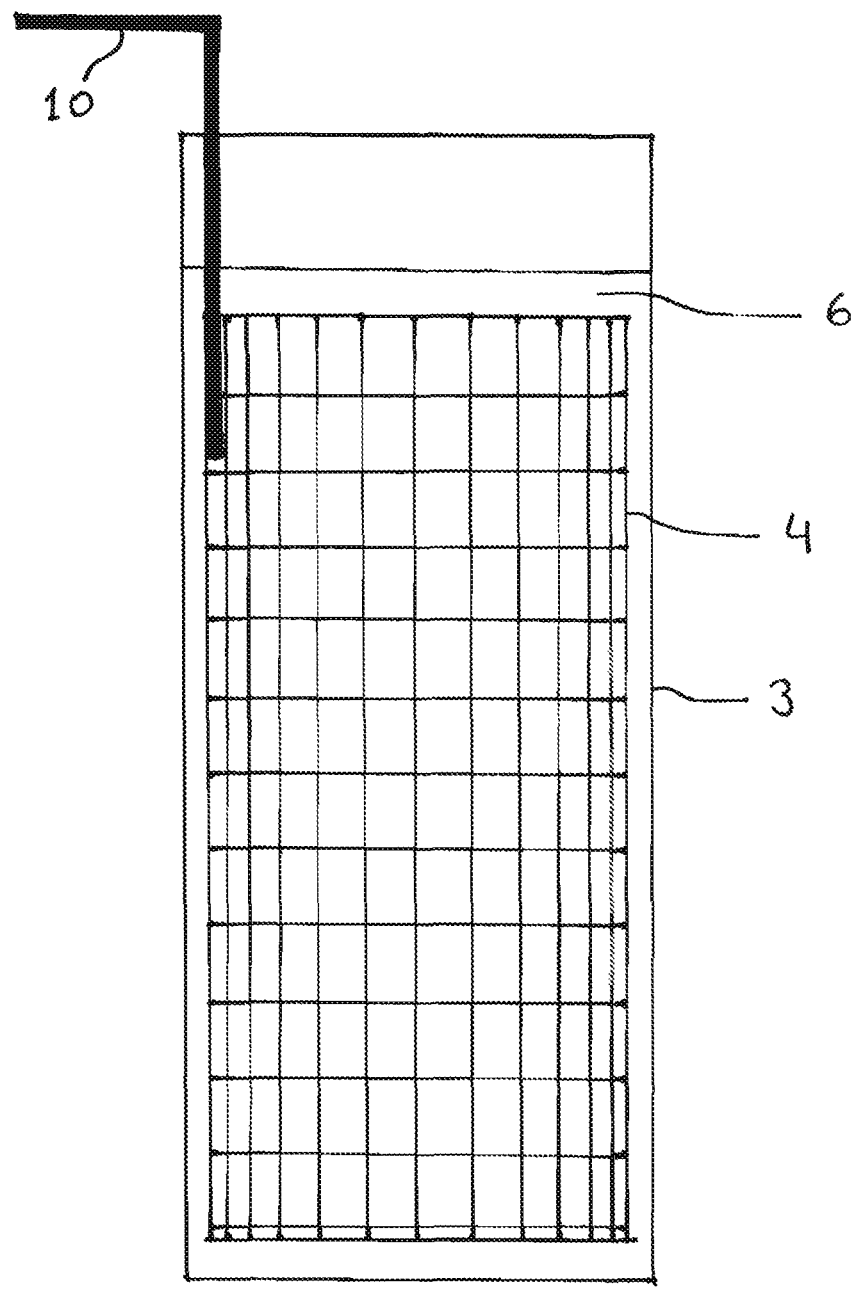

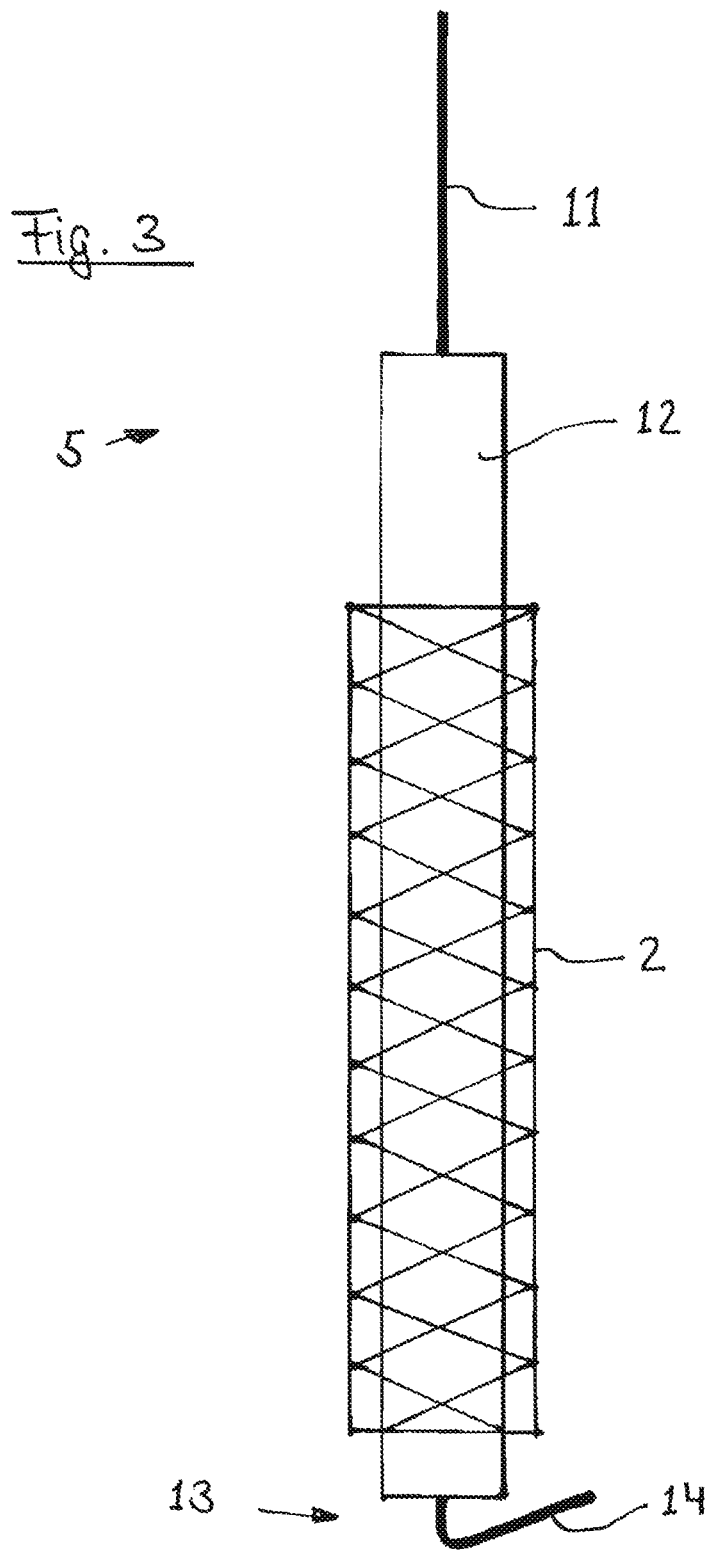

MEDICAL PRODUCT COMPRISING A CHITOSAN-COATED WALL AND METHOD FOR MANUFACTURING A MEDICAL PRODUCT

CROSS-REFERENCE TO RELATED APPLICATIONS

This application is a national stage application under 35 U.S.C. §371 of PCT Application No. PCT/EP2009/056685, filed May 29, 2009.

FIELD OF THE INVENTION

The invention relates to a method for manufacturing a medical product comprising a hollow body, wherein at least part of a wall of the hollow body is coated at least on the inside with a layer comprising a polymer. It further relates to a medical product comprising a hollow body with a wall consisting of one or more structural elements, at least a section of the wall being coated with a layer comprising native chitosan and a use of such medical product. Finally, the invention relates to a use of a medical product and a method for electrodepositing a polymer on an electrode from an acidic mixture.

BACKGROUND OF THE INVENTION

In many indications a medical product can be of advantage that comprises a hollow body, such as a medical stent, the wall of the hollow body being coated with a polymer, e.g. a polysaccharide such as chitosan.

A stent is a usually tubular object for insertion into a natural passage or conduit of the body, e.g. a blood-vessel, to prevent or counteract a localized flow constriction in said body passage or conduit. The wall of the stent often comprises a metal mesh, e.g. from metal wire, or a perforated metal sheet. Most stents are expandable in the sense that they can assume a compressed (or folded) state, in which they have a small tube cross-section for insertion into the body passage, and an expanded (or un-folded) state, which they can assume once introduced into the body passage and in which they have a larger cross-section in order to press against the walls of the body passage. The biocompatibility of medical products, in particular implantable medical products such as the before mentioned stents, can be improved by covering or coating them with a polymer, e.g. chitosan.

The polysaccharide chitosan is the N-deacetylated derivative of chitin, which can be found widely in the exoskeletons of arthropods, shells, crustaceans and the cuticles of insects. Chitosan, although naturally occurring in some fungi, is produced industrially by alkaline hydrolysis of chitin. The different solubilities of chitin and chitosan in dilute acids are commonly used to distinguish between the two polysaccharides. Chitosan, the soluble form, can have a degree of acetylation between 0% and about 60%, the upper limit depending on parameters such as processing conditions, molecular weight, and solvent characteristics. While soluble in acidic aqueous media, chitosan precipitates at a pH of above 6.3.

Both chitin and chitosan are promising polymers for a variety of applications, including water treatment (metal removal, flocculant/coagulant, filtration), pulp and paper (surface treatment, photographic paper, copy paper), cosmetics (make-up powder, nail polish, moisturizers, fixtures, bath lotion, face, hand and body creams, toothpaste, foam enhancing), biotechnology (enzyme immobilization, protein separation, chromatography, cell recovery, cell immobilization, glucose electrode), agriculture (seed coating, leaf coating, hydroponic/fertilizer, controlled agrochemical release), food (removal of dyes, solids and acids, preservatives, color stabilization, animal feed additive), and membranes (reverse osmosis, permeability control, solvent separation). Of particular interest are biomedical applications of chitin and chitosan because of their biocompatibility, biodegradability and structural similarity to the glycosaminoglycans. Applications and potential applications include wound dressings, tissue engineering applications, artificial kidney membranes, drug delivery systems, absorbable sutures, hemostats, antimicrobial applications, as well as applications in dentistry, orthopedics, ophthalmology, and plastic surgery. For comprehensive reviews of potential applications of chitin and chitosan see, for example Shigemasa and Minami, "Applications of chitin and chitosan for biomaterials" 1997, Biotech. Genetic. Eng. Rev. 1996, 13, 383, Kumar, "A review of chitin and chitosan applications", React. Funct. Polym. 2000, 46 (1), 1 and Singh and Ray, "Biomedical applications of chitin, chitosan, and their derivatives", J. Macromol. Sci. 2000, C40 (1), 69.

Due to its excellent biocompatibility, chitosan is a suitable candidate for biocompatible coatings in the medical field, such as for devices in urological, cardiovascular, gastrointestinal, neurological, lymphatic, otorhinolaryngological, ophthalmological and dental applications. For example, chitosan's regenerative potential towards endothelial cells (Chupa et al., "Vascular Cell Responses to Polysaccharide Materials: In Vitro and In Vivo Evaluations", Biomaterials 2000; 21 (22), 2315) supports the formation of blood compatible layers when chitosan is applied to the surface of cardiovascular implants (see Thierry et al., "Biodegradable membrane-covered stent from chitosan-based polymers", J. Biomed. Mater. Res. 2005; 75A (3); 556). Chitosan's bacteriostatic potential leads to a significant reduction of the risk of implant-related infections when applied as coating of vascular grafts (see Fujita et al., "Inhibition of vascular prosthetic graft infection using a photocrosslinkable chitosan hydrogel", J. Surg. Res. 2004, 121 (1), 135). Another advantage of chitosan coatings is the option to incorporate bioactive agents such as cytostatic drugs which can be released in a controlled fashion (see Chen et al., "The characteristics and in vivo suppression of neointimal formation with sirolimus-eluting polymeric stents", Biomaterials 2009, 30 (1), 79).

As to the coating of hollow medical products with polymers, the article by Thierry et al., supra, describes a method in which a metal stent is covered with a compact film by casting a jelly-like solution containing chitosan and polyethylene glycol onto the stent while the latter is rotated. The film covers the entire surface of the mesh-like stent, i.e. not only the struts but also the spaces between them. The latter can be disadvantageous as the chitosan layer between the struts may break when the stent changes from the compressed into the expanded state.

In the article "Feasibility evaluation of chitosan coatings on polyethylene tubing for biliary stent applications" by Lin et al., J. Appl. Poly. Sci. 2005, 97, 893-902 a method of manufacturing a biliary stent is described, in which a solid PE tube is covered on its inside with a chitosan layer. For this purpose, first a chitosan solution is injected into the tube and after one hour replaced with methanol. After removal of the methanol, the tube was dried, neutralized and further dried. It may be a disadvantage of this prior art method that it is not suitable for holey stents for the reason described above.

In the U.S. Pat. No. 7,279,174 a method is described in which a mixture of a hydrophobic polymer and a hydrophilic polymer such as chitosan is sprayed onto a stent in order to apply a chemically cross-linked networks of these polymers. It may be a disadvantage of this prior art that cross-linking and other modifications of chitosan can negatively affect the polymer's advantageous properties, in particular its biocompatibility. The U.S. Pat. No. 7,255,891 suggests dipping a stent into a polymer solution such as a chitosan solution or spraying it with that solution. Similarly, the U.S. Pat. No. 6,899,731 describes an experiment in which alternation layers of chitosan and DNA were applied to a balloon catheter by means of spraying or dipping. It is suggested that such alternating layers could also be applied to stents. The U.S. Pat. No. 6,555,225 discloses the formation of mechanically stable layers on a stent surface of a polyelectrolyte complex that comprises a water-soluble polyion such as chitosan iconically cross-linked to a water-insoluble polyion.

The U.S. Pat. No. 6,969,400 suggests applying to a synthetic implant such as a stent a mixture of chitosan and two other polymer components forming a covalently cross-linked network. In the U.S. Pat. No. 7,351,421 a method is described in which a chitosan solution is applied to a stent, e.g. by dip coating or spray coating, and a cross-linking agent is subsequently applied in order to covalently cross-link the chitosan. The U.S. Pat. Nos. 6,923,996 and 7,390,525 describe a method in which first a reactive layer comprising a cross-linking agent is applied on the surface of a medical device, such as a stent, followed by the application of a solution comprising a drug and a cross-linkable polymer, such as chitosan. Finally, the article by Thierry et al. "Bioactive coatings of endovascular stents based on polyelectrolyte multilayers", Biomacromolecules, 2003, 4 (6), 1564, describes a method in which a NiTi stent was first provided with a PEI primer layer and then alternating layers of hyaluronan and chitosan.

The article by Wu et al. "Voltage-dependent assembly of the polysaccharide chitosan onto an electrode surface", Langmuir, 2002, 18 (22), 8620, and the article by Fernandes et al. "Electrochemically induced deposition of a polysaccharide hydrogel onto a patterned surface" Langmuir, 2003, 19 (10), 4058 describe the electro-deposition of chitosan on negatively charged electrodes in an acidic aqueous chitosan solution. The U.S. Pat. Nos. 7,014,749 and 7,387,846 disclose methods for electrolytically depositing a mixture of chitin and brushite (a pre-cursor of hydroxyapatite) on a metallic prosthesis.

The international patent application WO 01/014617 describes an electrodeposition method in which a stent acting as working electrode, a reference electrode, and a counter-electrode are submerged in an electrolyte comprising chitosan. It is suggested that radioactively labelled chitosan may be deposited on the stent if the stent plays the role of the cathode. The inventors seek to exploit the fact that the presence of radioactivity on the surface of the stent can reduce the incidence of restenosis.

Problem to be Solved by the Inventions

It is an objective of the present invention to provide an improved method for manufacturing a medical product comprising a hollow body, wherein at least part of a wall of the hollow body is coated at least on the inside with a layer comprising a polymer. The invention further aims to provide an improved medical product comprising a hollow body with a wall consisting of one or more structural elements, at least a section of the wall being coated with a layer comprising native chitosan and a use of such medical product. Finally, it is an objective of the invention to provide an improved method for electrodepositing a polymer on an electrode from an acidic mixture of the polymer.

Solution According to the Invention

According to the invention, the problem is solved by a method for manufacturing a medical product comprising a hollow body, wherein at least part of a wall of the hollow body is coated at least on the inside with a layer comprising a polymer, wherein at least the part of the inside of the wall of the medical product brought into contact with a mixture, preferably a solution, of the polymer, and the polymer precipitates from the mixture to be deposited on at least the part of the inside of the wall. Moreover, the problem is solved by providing a medical product comprising a hollow body with a wall consisting of one or more structural elements, at least a section of the wall being coated with a layer comprising native chitosan, wherein both on the inside and the outside of the hollow body at least some of the one or more structural elements of the wall of the hollow body are at least partly coated with the native chitosan layer, and by the use of such medical product as a drug-eluting or non drug-eluting medical stent. Finally, the problem is solved by providing a method for electrodepositing a polymer on an electrode from an acidic mixture, preferably a solution, of the polymer, wherein the mixture comprises a multibasic acid, preferably citric acid.

In the context of the present invention, "coated" with regard to the wall of the hollow body means that the structural elements which make up the wall of the hollow body are coated with the polymer, while any apertures which may be present in the wall remain free. Apertures may occur e.g. if the wall is web- or mesh-like or from an expanded or perforated sheet of material, which is often the case in medical stents. In the case of a web- or mesh-like wall, the structural elements are the struts that border the apertures. If, on the other hand, the wall is compact, i.e. of a single, un-perforated piece, this piece is considered the wall's single structural element.

This is in contrast to a "covered" wall, which means that the wall is covered with a compact polymer layer, very much like a tent's frame is covered by the fabric of the tent. If a wall is "covered" by a polymer layer, the layer extends continuously across the wall, including any apertures which may be present in the wall. Because the compact layer extends across the apertures, the apertures in general will be closed by a polymer film. Note that such apertures in the wall need to be distinguished from openings in the medical product, such as the open end of a tubular stent. Reference to a "covered wall" does not in any way imply that such openings in the medical product also have to be covered by the polymer layer. In fact, quite to the contrary, these openings in general are uncovered. As far as in the following it is referred to merely a part of a wall rather than the entire wall, the above definition of the "coated" as distinguished from "covered" applies correspondingly.

For example, a mesh-like medical stent that is embedded in a compact tube of polymer with a polymer film extending across the apertures between the polymer-coated struts can be referred to as "polymer-covered", while a mesh-like medical stent in which a layer of polymer is only formed around the struts while keeping the apertures open can be referred to as "polymer-coated". It is an achievable advantage of the invention that due to the inside-coating of the medical product occlusions, including thrombosis, of a natural passage or conduit of the body, e.g. a blood vessel, in which the medical product is inserted, can be counteracted.

In the context of the present invention, the term "native chitosan" refers to the defined chemical entity chitosan, which is a poly(N-acetyl-D-glucosamine-co-D-glucosamine) copolymer. Any cross-linked or otherwise chemically modified chitosan is considered a chitosan derivative, having different properties than the native chitosan.

By coating rather than covering the wall of the medical product, it can advantageously be avoided that the polymer layer fractures when the medical product changes its shape, e.g. during an expansion of the kind that customarily occurs in a stent after it has been inserted. Also, advantageously, the area of the polymer layer can be minimized, thereby saving material and reducing adverse effects that can be induced by the presence of a foreign object inside the human or animal body, such as the occlusion of a body passage or conduit, including thrombosis and restenosis in a blood vessel.

It is an achievable advantage of the method according to the invention that a very thin layer can be achieved, thereby saving material and allowing for particularly flexible polymer layers. Moreover, particularly even polymer layers can be achieved which may add to the anti-occlusive properties of the coating.

It is another achievable advantage of the invention that it is suitable for coating hollow bodies from electro-conductive material, such as metal, with a polymer coating.

The invention advantageously can be applied to an implantable medical product such as a medical stent, including drug-eluting medical stents. Advantageously, the medical product may be applied in the medical treatment, e.g. in surgery or therapy or in diagnostic methods, of an animal, e.g. a mammal, in particular a human. It can in particular be applied to counteract an occlusion in a natural passage or a conduit of the animal or human body, such as in the cardiovascular system (e.g., coronary stent), biliary tract (e.g., biliary stent), gastrointestinal tract (e.g., esophageal stent), pulmonary tract (e.g., tracheal stent), or urinary tract (e.g., ureteral stent, urethral stent). Particularly advantageously, the medical product can be applied to prevent thrombosis.

It is an achievable advantage of the use of a citric acid-containing mixture in the electrodeposition of a polymer that the polymer layer obtained is smoother as compared to the prior art and/or pores in the layer can be avoided or at least reduced. While this is particularly useful in the method according to the present invention of manufacturing of the medical product, it is not limited to this application.

Preferred Embodiments of the Invention

In a preferred method according to the invention, the polymer precipitates from the mixture to be deposited on at least the part of the inside of the wall. Preferably, the medical product is at least partly immersed into the mixture of the polymer so that the inside and the outside of the wall are in contact with the mixture and the polymer is deposited from the mixture on at least the part of the inside and the outside of the wall. More preferably, the polymer precipitates from the mixture to be deposited on at least the part of the inside and the outside of the wall.

In a preferred embodiment of the invention, the wall of the hollow body is essentially tubular, preferably with an oval or circular cross-section. The hollow body may e.g. have the shape of a cylinder barrel, e.g. as typically in a cylindrical medical stent. It may, however, also have other tubular shapes, e.g. the pigtail-shape of a ureteral stent. The hollow body may also comprise several tubular branches, which may moreover differ in their cross sections. A medical product of this kind may e.g. be advantageously applicable as a branched medical stent.

The preferred medical product, more preferably the hollow body, has openings on its ends. Thereby it is achievable that a fluid, e.g. a body fluid such as blood, bile or urine, can flow through the medical product. The preferred medical product is a stent or an angioplastic device, i.e. any device used for angioplasty, preferably an angioplastic stent. Other preferred stents include biliary stents, esophageal stents, tracheal stents, ureteral stents, and urethral stents.

Preferably, at least part of the wall of the hollow body is holey, more preferably mesh- or web-like with apertures bordered by struts. In one preferred embodiment of the invention, the wall is a perforated or expanded sheet of material, in another, it is woven, e.g. from one or several strands of wire of material. The wall preferably comprises more than 20, more preferably more than 50, more preferably more than 100 apertures. The cross-section of the apertures preferably is between 0.5 μm (micrometers) and 5000 μm, more preferably between 10 μm and 2500 μm, more preferably between 50 μm and 1500 μm. The area of the solid part (i.e. the part made up by the structural elements as opposed to the apertures) of the wall of the hollow body, e.g. area of the struts in a mesh- or web-like wall, preferably is less than 75%, more preferably less than 50%, more preferably less than 25% of the overall wall area.

A preferred material of the wall is an electro-conductive material. The wall may be of a single material, preferably a metal or a metal alloy, or of several materials, preferably arranged in layers. In the latter case, at least the outermost layer, which layer is coated by the polymer according to the invention, preferably is of a metal or of a metal alloy. Preferred metals include silver, gold, platinum, palladium, iridium, osmium, rhodium, titanium, tungsten and ruthenium. Preferred metal alloys include cobalt-chromium alloys, nickel-titanium alloys (e.g. nitinol), iron-chromium alloys (e.g. stainless steel, which preferably contains at least 50% iron and at least 11.5% chromium), cobalt-chromium-iron alloys (e.g. elgiloy alloys), and nickel-chromium alloys (e.g. inconel alloys).

In one preferred embodiment of the invention, the coating comprises a single polymer, more preferably it consists of this polymer. The invention, however, also encompasses embodiments in which another substance, for example a biologically active substances such as a drug, is incorporated into the polymer. This other substance may of course also be a polymer. In a preferred embodiment of the invention, a metal or metal alloy, e.g. from the above list of metal and metal alloys, is incorporated into the polymer. Preferably, the mass fraction of the other substance to the total mass of the coating is less than 50%, more preferably less than 10% more preferably less than 1%. In a particularly preferred embodiment of the invention, the other substance is present in the coating only in traces, i.e. the mass fraction of the other substance to the total mass of the coating is less than 0.1%, more preferably less than 0.01%, more preferably less than 0.001%. The other substance may be present in the form of nanoparticles, i.e. particles with a diameter of less than 100 nanometers. The coating may of course also comprise several of the other substances. It is an achievable advantage of the presence of another substance or other substances in the coating that the medical product can be rendered a drug-eluting medical product, e.g. a drug-eluting medical stent. For example, a polymer coating comprising silver particles can release silver ions, which are known to have antibacterial properties. Moreover, the other substance(s) may provide the polymer layer with active groups to which further entities can attach.

Incorporation of the other substance may for example be achieved by providing the other substance in the mixture from which the polymer is deposited. It is also possible to introduce the other substance into the layer after the layer has already been formed, e.g. by immersing the polymer-coated wall into a mixture, e.g. a solution, of the other substance.

Alternatively or in addition, the medical product can be provided with a further layer into which the other substance(s), preferably including one or more drugs, are incorporated or which consists of the other substance(s). Again, this advantageously can render the medical product a drug-eluting medical product, e.g. a drug-eluting medical stent. The further layer preferably is applied before the polymer layer. The further layer preferably is located under the polymer layer.

The preferred polymer according to the invention is a polysaccharide. The preferred polymer is a biopolymer, i.e. a polymer that can be produced by a living organism. Preferably the biopolymer is a polymer that is formed by biological polymerisation, more preferably polymerisation of naturally occurring monomers. The polymer may be hydrophobic or hydrophilic. The preferred polymer with which the wall is coated is in its native form. In the context of the present invention, "native" with regard to the polymer means in particular that the polymer is not cross-linked, neither with itself nor with another polymer, chemically modified or chemically bound to another material. Preferably, the polymer of the coating is not ionized. Moreover, when the polymer is a biopolymer, it preferably is present in the coating in the form in that it usually occurs in nature.

A preferred polysaccharide is native chitosan. It is an achievable advantage of this embodiment of the invention that occlusions of the medical product can be avoided, presumably due to the biocompatibility of the native chitosan, its regenerative potential towards endothelial cells and/or its bacteriostatic potential. Moreover, advantageously, bioactive agents such as drugs can be incorporated into the native chitosan coating.

Suitable non-native polymers include derivatives of chitosan, e.g. partially or fully N—, O—, or N,O-derivatized chitosan, including derivatives capable of forming a positive charge such as those bearing amine, guanidinium, imidazole, indole, purine, pyrimidine, pyrrole, etc. functionalities, as well a derivatives capable of forming a negative charge such as those bearing alkoxide, carboxyl, carboxylate, hydroxy acid, phenolic, phosphate, sulfhydryl, etc. functionalities. Other suitable polymers include polysaccharides, polypyrrols, polyamines, polyimines, polypeptides, polyamino acids, polycarboxylic acids as well as other polymers and polymer derivatives capable of forming a positive or negative charge.

In a preferred medical product according to the invention, the entire wall is coated with the polymer, at least on one side, preferably on both sides.

In a preferred medical product, at least a section of the wall, preferably the entire wall, is coated on both sides with the polymer layer such that the coating continuously extends from the inside to the outside of the hollow body. In other words, there is no un-coated gap between the outside and the inside coating of the (part of the) wall of the hollow body. Preferably, the coating will extend from the inside to the outside of the hollow body through the apertures in the wall.

In a preferred medical product, at least some of the one or more structural elements which make up the wall of the hollow body will be entirely coated with the polymer layer. In this context, "entirely coated" means in particular that if a structural element has a part on the inside and another part on the outside of the hollow body, there is no gap between the coating of the structural element on the inside part and the coating of the structural element on the outside part. Rather, the coating continuously extends on the structural element from the inside to the outside of the hollow body. Preferably all of the structural elements which make up a section, more preferably all structural elements which make up the entire wall of the hollow body, will be entirely coated with the polymer layer.

In a preferred method according to the invention, at least the entire inside of the wall of the medical product is brought into contact with the mixture of the polymer and the polymer precipitates from the mixture to be deposited at least on the inside of the wall. It is an achievable advantage of this embodiment of the invention that the entire wall of the hollow body is coated at least on the inside with the polymer.

In a preferred method according to the invention, the medical product is at least partly, more preferably entirely, immersed into a mixture of the polymer so that the inside and the outside of the wall are in contact with the mixture and the polymer precipitates from the mixture in order to be deposited on at least the part of the inside and the outside of the wall. It is an achievable advantage of this embodiment of the invention, that the wall of the hollow body can be polymer-coated both on the inside and the outside, preferably simultaneously.

The thickness of the coating may be the same on the inside and the outside or the thickness on the inside is different to that on the outside. If the thicknesses are different, the inside coating preferably is thicker than the outside coating. Preferably, the thickness of the polymer coating on the inside of the hollow body is between 0.02 µm and 2000 µm, more preferably between 0.2 µm and 200 µm, more preferably between 0.5 µm and 10 µm. The preferred thickness of the polymer coating on the outside of the hollow body is between 0.02 µm and 2000 µm, more preferably between 0.2 µm and 200 µm, more preferably between 0.5 µm and 10 µm.

In the context of the present invention, the "thickness" of the coating is measured in the direction perpendicularly to the surface of the coated structural element. It is an achievable advantage of the invention that very even coatings can be achieved. In particular, accumulations of coating polymer that extend from the structural elements into the apertures can be avoided, such as accumulations that have the shape of webbings that extend from struts of a web- or mesh-like wall into the apertures surrounded by the struts. According to the present definition of "thickness", the parts of the structural elements from which these accumulations extend would have a much thicker coating than the surrounding parts. In contrast to this, in a preferred embodiment of the invention the difference in thickness between a local minimum and an adjacent local maximum of thickness on the same side of the hollow body is less than 100%, more preferably less than 30%, more preferably less than 10%, more preferably less than 3%, more preferably less than 1% of the average thickness of the polymer layer on this side of the hollow body.

In a preferred method according to the present invention, the deposition of the polymer more specifically is an electrodeposition; in other words, the polymer is electrodeposited on the wall. Electrodeposition involves the application of an electric current through the mixture by means of at least two electrodes of opposite polarity. Further information on electrodeposition can be found in the "Handbook of nanophase and nanostructured materials" Vol. 1, "Synthesis" by Zhong Lin Wang et al., Kluvers. In a suspension or colloid, the electrodeposition may more specifically be an electrophoretic deposition (EPD).

Preferably, the hollow body serves as one electrode and has a polarity opposite to that of a counter-electrode, which is also at least partly immersed into the mixture. In a preferred embodiment of the invention, an electrode is placed on the outside of the hollow body (outside electrode). The outside electrode may e.g. be an electro-conductive mesh, preferably from metal. It preferably surrounds the entire hollow body.

In a preferred embodiment of the method according to the present invention at least one electrode is placed inside the hollow body (inside electrode). The inventors have found that advantageously placing one electrode on the inside of the hollow body can improve the electrodeposition of polymer on the inside of the hollow body. Preferably the inside electrode has the same polarity as the hollow body, more preferably the inside electrode is electrically connected to the hollow body. In a preferred embodiment, the inside electrode doubles as a support, e.g. a hanger, for the hollow body. For this purpose, part of the inside electrode may be hook-shaped. The part of the inside electrode that acts as a support is preferably electrically conducting. It is an achievable advantage of this embodiment of the invention that in a convenient and reliable manner an electrical contact can be realised between the inside electrode and the hollow body to ensure that both have the same polarity.

In an alternative embodiment, the inside electrode has a polarity opposite to that of the hollow body, i.e. it acts as a counter electrode. In this case, preferably appropriate measures are taken to ensure that the inside electrode does not come into contact with the hollow body. Thereby, advantageously, a shortcut between the hollow object and the inside electrode can be avoided. For this purpose, the inside electrode may e.g. be provided with a porous varnish coating as suggested in the German patent DE 758374 B. If the inside electrode doubles as a hanger, e.g. by means of a hook-shaped part as discussed above, this part is preferably non-conductive or insulated.

The preferred inside electrode is elongated, preferably extending at least through part of the inside of the hollow body, more preferably extending through the entire inside of the hollow body. E.g., if the hollow body is tubular, the preferred inside electrode extends from one tube opening to the other tube opening. Preferably, the hollow body is placed essentially vertically in the mixture. In this case, the preferred inside electrode also extends vertically through the inside of the hollow body, the bottom part of the inside electrode preferably supporting the hollow body in the mixture and at the same time electrically contacting the hollow body.

The inside electrode may e.g. comprise an electro-conductive wire or a tube such as a cannula, preferably from metal. In a preferred embodiment of the invention, the inside electrode comprises a metal tube slid over a metal wire. The inside electrode preferably has an outer diameter between 5% and 95%, more preferably between 50% and 90%, more preferably between 60% and 80% of the inner diameter of the hollow body to be coated.

Preferably, the mixture of the polymer more specifically is a solution of the polymer, in other words, the polymer is dissolved in a solvent. The invention, however, also encompasses embodiments, in which the mixture is a colloid or a suspension, or more generally, a dispersion, i.e. the polymer is merely suspended in a mixture medium. The mixture medium, i.e. for example the solvent or the dispersion medium, preferably is a liquid.

In a preferred method according to the invention, the polymer is electrically charged in its mixed state, i.e. for example in its dissolved or dispersed state. The preferred polymer is a cation in the mixture. However, the invention of course also encompasses embodiments in which the polymer is an anion in the mixture. Preferably, during electrodeposition, the hollow body acting as an electrode is oppositely charged to the polymer ion in the mixture, more preferably negatively charged, acting as a cathode. Thus advantageously, charged ions of the polymer can be attracted by the hollow body.

The preferred mixture medium comprises a protic solvent or a polar aprotic solvent. The mixture may comprise a single mixture medium, preferably water, or a combination of mixture media, one of which preferably is a polar aprotic solvent or a protic solvent, preferably water. Advantageously, water is a good solvent for ions, inexpensive, and well compatible with medical applications.

During deposition, in a preferred embodiment of the invention, the polymer precipitates from the mixture due to charge destruction, preferably near the inside and/or outside of the hollow body. For example, in an aqueous mixture charge destruction can be induced by an increase of pH near the hollow body if the latter acts as a cathode, or a decrease of pH near the hollow body if the latter acts as an anode. To adjust the pH of the mixture, it preferably further comprises an acid or a base. Preferred acids include inorganic acids, such as hydrochloric acid, as well as organic acids selected from the group of monobasic or multibasic organic acids having 2 to 12 carbon atoms and a first pKa value between 1 and 5, such as citric acid, lactic acid, malic acid, succinic acid, mandelic acid, oxalic acid, tartaric acid, ascorbic acid, etc. Mixtures of inorganic and organic acids, as well as salts of inorganic and organic acids (e.g., buffered solutions) may be used as well to adjust the pH of the mixture.

A preferred polymer-layer is essentially pore-free. A preferred acid is a multibasic acid, eg, citric acid. With this embodiment a particularly smooth layer of polymer can be deposited on the electrode and/or pores in the polymer layer can be avoided or at least reduced.

In a preferred embodiment of the invention, the bulk of the polymer mixture is acidic, with a pH preferably between −1.0 and 6.5, more preferably between 1.0 and 6.0, more preferably between 3.0 and 5.5. It is an achievable advantage of this embodiment of the invention that polymers such as chitosan are soluble in the bulk of the mixture, but can precipitate from the mixture near the hollow body if the latter acts as a cathode, due to the increased pH near the cathode.

Preferably, the polymer is present in the mixture at a concentration between 0.01% and 10%, more preferably between 0.1% and 1%, e.g. 0.33%. The voltage applied to the electrodes for electrodeposition preferably is chosen from a range between 0.1 and 50 V (Volts), more preferably between 1 and 15 V, e.g. 10 V. The voltage preferably is applied for between 0.1 and 300 s (seconds), more preferably between 1 and 60 s, e.g. 15 s. The thickness of the layer achieved greatly depends on the time the voltage is applied and can thus be adjusted by an appropriate choice of this duration. For example, applying a voltage of 10 V for 15 s results in a chitosan layer of appr. 1 μm. As a general rule, higher polymer concentrations, as well as higher voltage and/or longer application times result in thicker layers deposited. To achieve the desired layer thickness, these parameters may be adjusted depending on the design of the hollow body to be coated. However, very high voltages and/or long application times may result in increased layer roughness and porosity, due to the formation of gas bubbles during the electrolytic process. High polymer concentrations, on the other side, result in increased mixture viscosities, thereby increasing the probability of layer formation between the structural elements (i.e., coverings) of the hollow body.

BRIEF DESCRIPTION OF THE DRAWINGS

The invention is illustrated in greater detail with the aid of schematic drawings.

FIG. 1 shows schematically a set-up for manufacturing a mesh-like vascular stent according to the invention with a chitosan coating by means of electrodeposition;

FIG. 2 shows schematically the container and the counter-electrode of the set-up of FIG. 1;

FIG. 3 shows schematically the working electrode and inner electrode combination of the set-up of FIG. 1;

DETAILED DESCRIPTION OF EMBODIMENTS OF THE INVENTION

EXAMPLE 1

Figure 7:
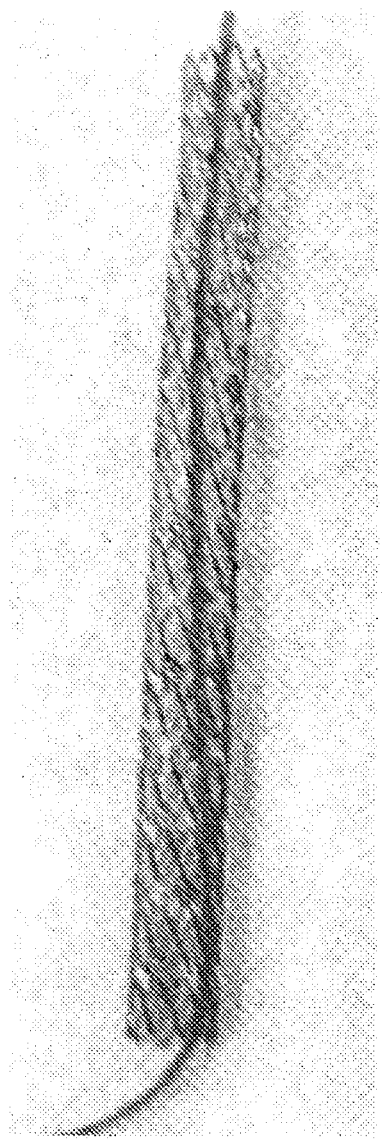
FIGS. 4-10 show photographs of vascular stents obtained with the set-up of FIG. 1 under various conditions.

A set-up 1 for coating the mesh-like wall of a hollow cylindrical stent 2 with a chitosan layer both on the inside and the outside is schematically shown in FIG. 1. It essentially comprises a cylindrical container 3 and an outer electrode 4, the stent 2, and an inner electrode 5 immersed into a chitosan containing solution 6 in the container 3. The outer electrode 4 serves as the counter-electrode, being connected to the positive pole 7 of a power supply 8, while the stent 2 and the inner electrode 5 are connected to each other and to the negative pole 9 of the power supply 8.

FIG. 2 shows the container 3 with the solution 6 and the outer electrode 4 of the set-up 1. The container 3 is a vertical glass cylinder of circular cross-section and a diameter of approx. 5 cm (centimeters) having an inner volume of approx. 100 ml (milliliters), holding approx. 80 ml of solution 6. Immersed into the solution 6 is a cylindrical grid of stainless steel which runs along the inside wall of the glass cylinder on its entire circumference and acts as the outer electrode 4. The cylindrical grid's diameter is approx. 4 cm, its mesh size is approx. 3 mm (millimeters). The wires of which the grid is made have a thickness of approx. 0.5 mm. Moreover, a wire 10 of stainless steel connects the cylindrical grid with the outside of the cylindrical glass container.

As shown in FIG. 3, the inner electrode 5 of the set-up 1 comprises an approx. 20 cm long stainless steel wire 11 with a diameter of approx. 0.3 mm, and a 5 cm long blunt stainless steel cannula 12 slid over the wire 11. At the bottom 12, the wire 11 is bent in a hook-like fashion, so that the cannula 12 is supported at the bottom 12 of the wire 11 when the wire 11 is held in a vertical position, as shown in FIG. 1.

The stent 2 is a bare metal coronary stent made of stainless steel. The stent 2 has the shape of a circular cylinder with a length of approx. 39 mm and a diameter of approx. 1.55 mm. The stent's wall comprises of struts 16 with an essentially square-shaped cross-section, the sides of the square having a length about 100 µm, which is consequently also the width of the stent's 2 wall. The stent 2 is slid over the cannula 12, and the hook-shaped part 14 of the wire 11 is large enough to also support the stent 2 when the entire arrangement 2, 5 is brought into a vertical position. The arrangement of stent 2 and inner electrode 5 is placed into the solution 6 near the centre of the cylindrical glass container 3 such that the stent 2 is fully immersed in the solution 6. The wire 11 is electrically connected to the negative pole 9 of the power supply 8. As both the cannula 12 and the stent 2 sit on the hook-shaped part 14 of the wire 11, they are, too, connected to the negative pole 9 of the power supply 8 and thus have the same polarity. The outer electrode 4 is electrically connected to the positive pole 7 of the power supply 8. Then, through the power supply 8, a voltage of 10 V is applied between the counter-electrode and the metal wire for an appropriate amount of time, e.g. 15 s.

Afterwards, the wire 11 is disconnected from the power supply 8 and the arrangement of wire 11, cannula 12, and stent 2 is removed from the solution 6 using tweezers and placed in a hanging position in a bath of distilled water (pH 7). Further by means of the tweezers, the cannula 12 is gently removed while the stent 2 remains sitting on the wire 11. Then, the bath of distilled water is agitated (by means of stirring at 200 rpm) for approximately 2 min (minutes) to wash the chitosan-coated stent.

To make the chitosan coating visible for inspection, the chitosan is subsequently stained by immersing it into a staining solution. The staining solution comprises a 0.1% aqueous solution of indigocarmine. After an incubation time of approximately 1 min in the staining solution, the stent 2 is removed and dipped in distilled water for 10 s and then left hanging to dry at room temperature under vacuum. Finally, the stent 2 is removed from the wire 11 and is kept in a dust-free environment. In a variation of this procedure, the cannula 12 is kept on the wire 11 during the entire procedure above and is only removed from the stent 2 together with the wire 11 at the end of the procedure.

Figure 4:
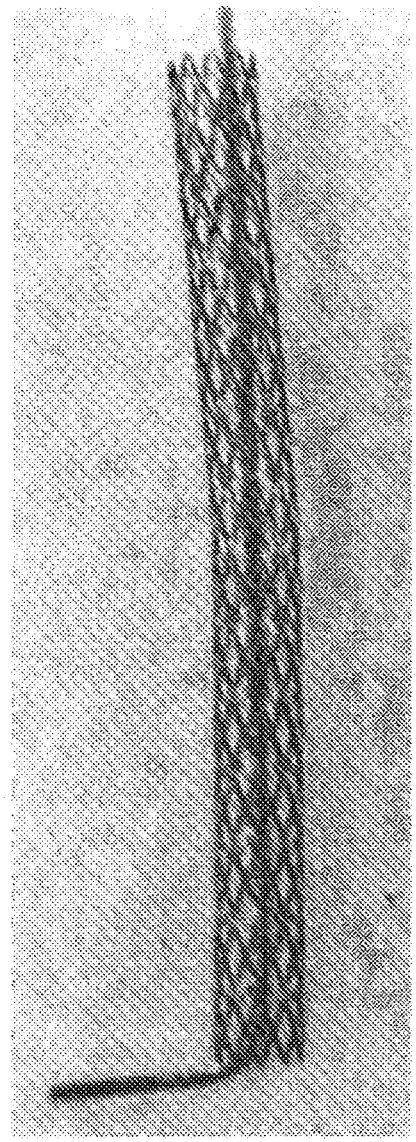
Figure 6:
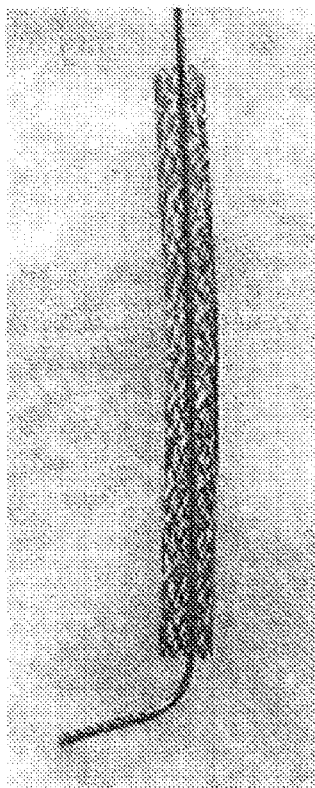
Figure 5:
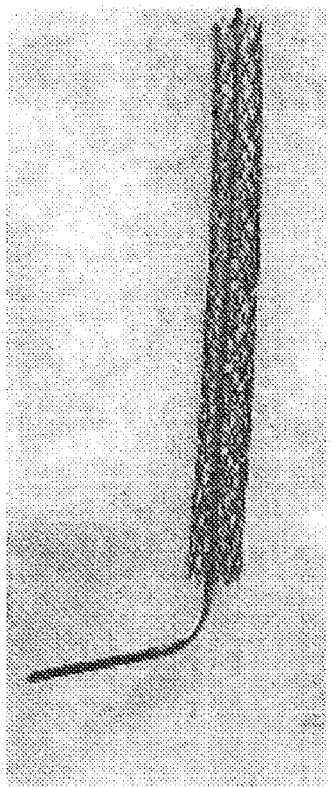

FIGS. 4 to 10 show the result of various coating experiments under different conditions. In all experiments, a voltage of 10 V was applied for 15 s. As can be seen from the experiments, the diameter of the cannula as well as the choice of acid have an important impact on the coating obtained. In FIGS. 4 and 5, citric acid was used as the acid in a solution 6 of the following composition: 0.33% of chitosan in 1% citric acid solution mixed with N-methyl pyrrolidone (1:1). The cannula 12 had a diameter of 1.18 mm (FIG. 4) and 1.38 mm (FIG. 5), respectively. A good coating both on the inside and the outside of the stent 2 was observed.

Figure 8:
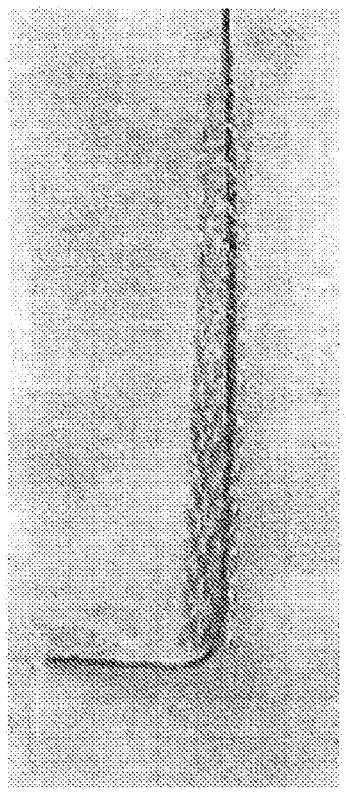

In contrast, a 0.81 mm cannula 12 under otherwise identical conditions yielded merely a good outside coating but no observable coating on the inside (FIG. 8). Similarly, when instead of a cannula 12 only a 1.15 mm wire 11 was used as the inside electrode, only a weak and irregular coating on the outside and no observable coating on the inside was achieved (FIG. 7). The effect of the choice of acid in the solution 6 is demonstrated in FIG. 8, where under otherwise identical conditions to those of FIG. 4 a solution comprising 1% acetic acid was used instead of citric acid. No coating was observable under these conditions.

Figure 9:
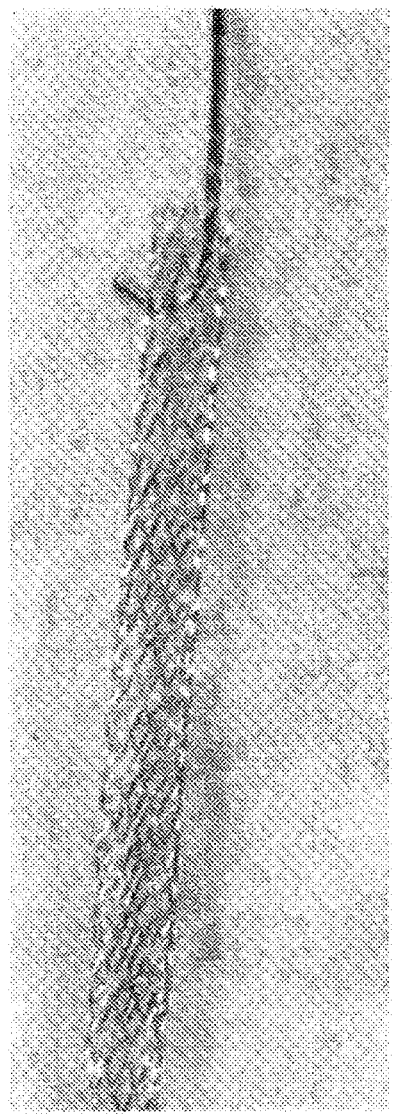
Figure 10:
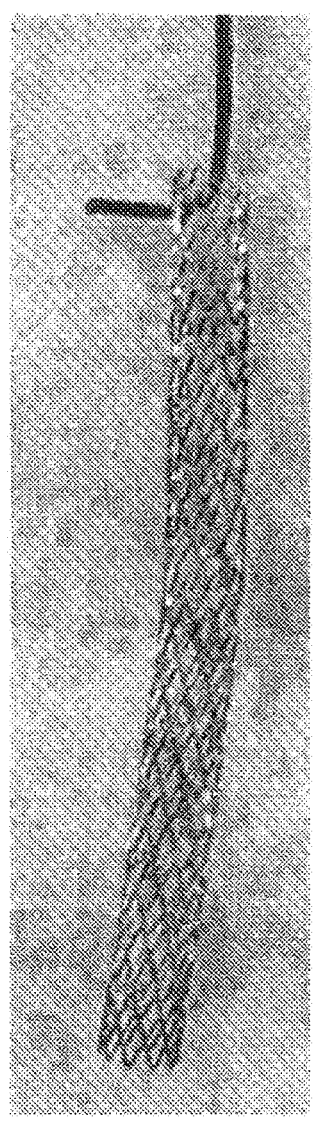
Figure 11:
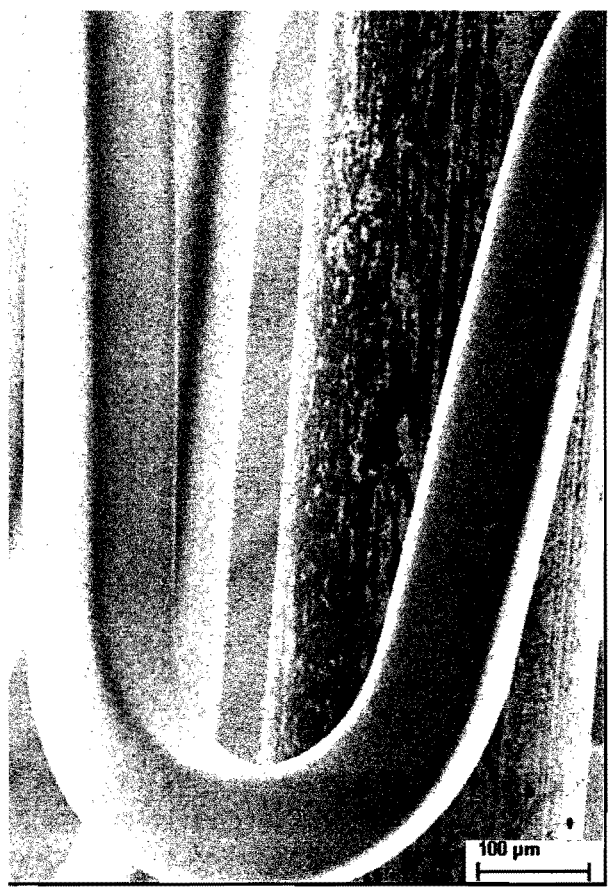
FIG. 11 shows an SEM image of a section of a coated stent.
Figure 12:
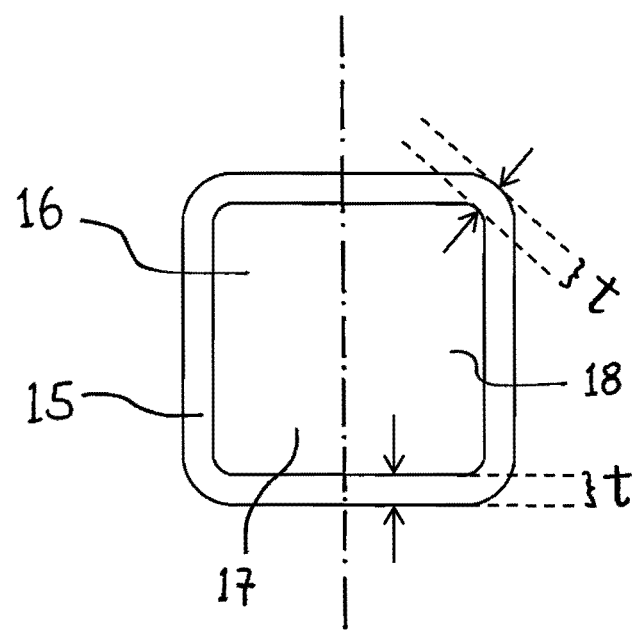
FIG. 12 shows schematically a cross-section through the wall of a polymer-covered stent.

FIGS. 9 and 10 show control experiments in which no inner electrode 5 was present at all. Rather, the stent 2 was supported at its top by the hook-shaped end 14 of the metal wire 11 so that the wire did not traverse the inner of the stent 2. In a chitosan solution that contained acetic acid (the composition comprising 0.33% of chitosan in 1% acetic acid solution mixed with N-methyl pyrrolidone (1:1)), no coating was observed at all while when citric acid was used (the composition comprising 0.33% of chitosan in 1% citric acid solution mixed with N-methyl pyrrolidone (1:1)) there was a weak coating only on the outside of the stent. As can be seen from FIG. 11, which shows a scanning electron-micrograph of a section of a stent 2 obtained under the conditions of example 1, the coating obtained is very even, without any pores or spikes. In particular, no webbings can be observed that extend into the apertures between the webs. Finally, by means of a schematic cross-section through the stent 2, FIG. 12 illustrates that the local thickness t of the coating layer 15 on a structural element 16 of the wall is measured in the direction perpendicularly to the surface of the coated structural element 16. The structural element 16 has a part 17 on the inside of the hollow body and a part 18 in the outside of the hollow body. It is entirely coated with the coating layer 15 in the sense that there is no gap between the coating of the structural element on the inside part 17 and the coating of the structural element on the outside part 18. Rather, the coating layer 15 continuously extends on the structural element 16 from the inside to the outside of the hollow body.

EXAMPLE 2

This is an example of incorporating an additive such as a drug by coating from a chitosan/additive suspension 6. Diflunisal is used as a model drug. The stent 2 is coated following the steps as described in Example 1 above, except that the chitosan solution 6 comprised of 0.33% chitosan, 2% citric acid, and 0.33% diflunisal which was suspended in the chitosan solution using an Ika T25 Ultra-Turrax homogenizer at 24000 rpm for appr. 30 s.

EXAMPLE 3

This is another example of incorporating an additive such as a drug by coating from a chitosan/additive solution 6. Diflunisal is used as a model drug. The stent is coated following the steps as described in Example 1, except that the chitosan solution 6 comprised of 0.33% chitosan, 1% citric acid/N-methylpyrrolidone (1:1), and 0.33% diflunisal.

EXAMPLE 4

This is yet another example of incorporating an additive such as a drug by first forming a layer of the additive, followed by coating from a chitosan solution 6. Diflunisal is used as a model drug. The stent 2 as used in Example 1 is dip-coated in a 5% solution of diflunisal in acetone, and after drying for approx. 5 min, coated following the steps as described in Example 1, except that the chitosan solution 6 comprised of 0.33% chitosan and 2% citric acid.

EXAMPLE 5

This is yet another example of incorporating an additive such as a drug by first coating from a chitosan solution 6, followed by immersion in a drug solution. Diflunisal is used as a model drug. A stent 2 is coated as described in example 1, followed by immersion in a solution of 0.5% diflunisal in 0.1 N sodium hydroxide for approx. 10 min. Afterwards, the stent 2 is washed thoroughly in distilled water, dried at room temperature and stored in a dust-free container.

The features described in the above description, claims and figures can be relevant to the invention in any combination. The reference numerals in the claims have merely been introduced to facilitate reading of the claims. They are by no means meant to be limiting.

The invention claimed is:

1. A method for manufacturing a medical product comprising a hollow body, wherein at least part of a wall of the hollow body is coated at least on the inside with a layer comprising a polymer, wherein at least the part of at least the inside of the wall of the medical product is brought into contact with a mixture of the polymer and the polymer is electrodeposited from the mixture on at least the part of the inside of the wall, and wherein at least one electrode is placed inside the hollow body.

2. The method according to claim 1, wherein the medical product is at least partly immersed into the mixture of the polymer so that the inside and the outside of the wall are in contact with the mixture and the polymer is deposited from the mixture on at least the part of the inside and the outside of the wall.

3. The method according to claim 1, wherein at least part of the wall of the hollow body is holey.

4. The method according to claim 1, wherein the inside electrode has the same polarity as the hollow body.

5. The method according to claim 1, wherein the polymer in its mixed state is electrically charged.

6. The method according to claim 1, wherein the polymer is a polysaccharide.

7. The method according to claim 1, wherein an additive or a drug is incorporated into the layer formed by the polymer that is deposited on at least the part of the wall, or the additive or the drug forms or is incorporated into another layer applied to the medical product.

8. The method according to claim 1, wherein the polymer is native chitosan.

* * * * *